United States Patent [19]

Masuho et al.

[11] Patent Number: 5,298,419
[45] Date of Patent: Mar. 29, 1994

[54] HUMAN HYBRIDOMAS AND MONOCLONAL ANTIBODIES WHICH BIND BOTH GP41 AND GP120 ENVELOPE PROTEINS OF HUMAN IMMUNODEFICIENCY VIRUS

[75] Inventors: Yasuhiko Masuho; Toru Sugano; Yoh-ichi Matsumoto, all of Tokyo, Japan; Evan M. Hersh; Eskild A. Peterson, both of Tucson, Ariz.

[73] Assignees: The Arizona Board of Regents on behalf of the University of Arizona, Tucson, Ariz.; Teijin Limited, Osaka, Japan

[21] Appl. No.: 176,159

[22] Filed: Mar. 31, 1988

[51] Int. Cl.⁵ .................. C12N 5/24; C07K 15/28; A61K 39/42
[52] U.S. Cl. .................. 435/240.27; 424/86; 435/5; 435/70.21; 435/172.2; 530/388.15; 530/388.35
[58] Field of Search ............ 435/240.27, 172.2, 70.21, 435/5; 530/387, 388.15, 388.35; 424/87, 88, 89, 85.8, 86

[56] References Cited

U.S. PATENT DOCUMENTS 4,363,799 12/1982 Kung et al. ............... 424/85.8
4,515,894 5/1985 Kung et al. ............... 435/240.27
5,087,557 2/1992 McClure .................. 435/5

FOREIGN PATENT DOCUMENTS 0251612 6/1987 PCT Int'l Appl. .

OTHER PUBLICATIONS

Matthews et al., Proc. Natl. Acad. Sci. USA 83(24):9709-9713, Dec., 1986.
Abrams et al., Methods in Enzymology, 121:107-119, 1986.
Foung, Chem. Abs. 110:55817s.
Grunow, J. Imm Mtds (1988) 106:257-265.
Banapour, J. Immunol (Dec. 1987) 139:4027-4033.
Dreesman, J Cell Biochem (Mar. 29-May 1, 1987) Suppl 1D, Abs p014, p. 34.
Gosting, J. Clin. Microbiol (May 1987) 25(5): 845-848.
McDougal et al., J. Cellular Biochemistry (Mar. 29-May 1, 1987) Suppl 11D, Abstract P018, p. 36, Alan R. Liss, Inc., N.Y.
Chanh et al., Eur. J. Immunol., (1986) 16:1465-1468.
Larrick et al., chp 9 in Human Hybridomas and Monoclonal Antibodies.
Engleman, Foung, Larrick & Raubitschek (ed) Plenum Press, 114(1985) pp. 149-165.
Kennedy et al., J. Biol. Chem. (Apr. 1987) 262(12):5769-74.
Lasky et al., Science (Jul. 1986) 233:209-212.
Roitt et al., Chapter 5 in Immunology (1985) 5.1-5.10.
Roitt, Brostoff & Male (eds) Gower Medical Publishing New York.
Journal of Immunological Methods, (1988), vol. 106, pp. 257-265, "The High Efficiency, Human B Cell Immortalizing Heteromyeloma CB-57", R. Grunow et al.
Monoclonal Antibody-Production Techniques and Applications, (1987), vol. 33, pp. 51-63, "Mouse-Human Myeloma Partners for the Production . . . " B. Brodeur et al.
Biochemical and Biophysical Research Communications, (1988), vol. 155, pp. 1105-1112, "Human Monoclonal Antibody Glycoproteins . . . " T. Sugano et al.
Journal of Immunology, (1988), vol. 140, pp. 941-943, "Human Monoclonal Antibody Directed Agains gag Gene Products of the Human . . . " L. Evans et al.

(List continued on next page.)

Primary Examiner—David L. Lacey
Assistant Examiner—Robert D. Budens
Attorney, Agent, or Firm—Oblon, Spivak, McClelland, Maier & Neustadt

[57] ABSTRACT

The invention is directed to the human hybridoma designated MCA 86 and having A.T.C.C. Accession No. HB 9669 and human monoclonal antibodies produced by hybridoma MCA 86. Human monoclonal antibodies produced by hybridoma MCA 86 immunologically binds to both gp41 and gp120 envelope glycoproteins of Human Immunodeficiency Virus (HIV). These monoclonal antibodies are useful in the diagnosis of HIV infection.

2 Claims, 2 Drawing Sheets

OTHER PUBLICATIONS

*Journal of Immunology,* (1987), vol. 139, pp. 4027–4033, "Characterization and Epitope Mapping of a Human Monoclonal Antibody Reactive with . . . " B. Banapour et al.

*Journal of Clinical Microbiology,* (1987), vol. 25, pp. 845–848, "Monoclonal Antibodies to gp110 and gp41 of Human Immunodeficiency virus". Gosting et al.

*Chemical Abstracts,* 108:54050h, Characterization and epitope mapping of a human monoclonal antibody reactive with the envelope glycoprotein of human immunodeficiency virus, Banapour.

*Chemical Abstracts,* 108:166098m, Immortalized cells which produce tissue-specific products and their formations, Foung.

*Chemical Abstracts,* 110:55817s, Immortalized virus-specific tissue cells, their preparation and uses, Foung.

*Chemical Abstracts,* 112:19784m, CD4 antigen-based antireceptor peptides inhibit infectivity of human immunodeficiency virus in vitro at multiple stages of the viral life cycle. Nara.

*Chemical Abstracts,* 105:207285d, Induction of CD4-dependent cell fusion by the HTLV-III/LAV envelope glycoprotein. Lifson.

*Chemical Abstracts,* 106:46942u, Role of envelope glycoprotein carbohydrate in human immunodeficiency virus (HIV) infectivity and virus-induced cell fusion, Lifson.

Biochemical & Biophysical Research Communications, vol. 137, No. 1, May 29, 1986, pp. 273–280, Y. Matsumoto, et al., "Generation of Hybridomas Producing Human Monoclonal Antibodies Against Human Cytomegalovirus".

Biochemical & Biophysical Research Communications, vol. 135, No. 2, Mar. 13, 1986, pp. 495–500, Y. Masuho, et al., "Generation of Hybridomas Producing Human Monoclonal Antibodies Against Herpes Simplex Virus after in Vitro Stimulation".

Eur. J. Immonol., 1987, 17, pp. 359–364, T. Sugano, et al., "Hybridomas Producing Human Monoclonal Antibodies Against Varicella-Zoster Virus".

Journal of General Microbiology, vol. 133, 1987, pp. 3581–3590, S. Sawada, et al., "Immunoprotective Human Monoclonal Antibodies Against Five Major Serotypes of Pseudomonas Aeruginosa".

The Journal of Infectious Diseases, vol. 152, No. 5, pp. 965–970, Nov. 1985, S. Sawada, et al., "Characterization of a Human Monoclonal Antibody to Lipopolysaccharides of Pseudomonas Aeruginosa Serotype 5: A Possible Candidate as an . . . ".

J. Gen. Virol., vol. 68, 1987, pp. 1457–1461, Y. Masuho, et al., "Human Monoclonal Antibodies Neutralizing Human Cytomegalovirus".

HIV VIRAL STRUCTURE

HUMAN HYBRIDOMAS AND MONOCLONAL ANTIBODIES WHICH BIND BOTH GP41 AND GP120 ENVELOPE PROTEINS OF HUMAN IMMUNODEFICIENCY VIRUS

FIELD OF THE INVENTION

The present invention relates to human monoclonal antibodies (abbreviated as MCAs hereinafter) specific for human immunodeficiency virus (abbreviated as HIV herein), and hybridomas which produce these MCAs. The human MCAs of this invention are specific for HIV and will be useful in the diagnosis, prevention and therapy of HIV infection.

DESCRIPTION OF THE BACKGROUND

HIV is a virus which primarily infects helper T lymphocytes and ultimately destroys them, resulting in extreme immunological failure known as AIDS (acquired immunodeficiency syndrome). In the early stages of HIV infection, some patients develop symptoms which resemble those of infectious mononucleosis, i.e., fever, fatigue, headache, etc. Subsequently, although the patient becomes asymptomatic, he/she becomes a carrier of anti-HIV antibodies in the blood. Then, after a latent period lasting up to a number of years, the patient develops AIDS-related complex (ARC). ARC patients exhibit various symptoms such as systemic swelling of lymph nodes, fever, general fatigue, weight loss, decreased platelet and lymphocyte levels, etc. As the disease progresses, the patient becomes susceptible to and often develops Kaposi's sarcoma and various opportunistic infections such as *Pneumocystis carinii* pneumonia, fungal infections, cytomegalovirus infection, etc., which end in death. The most striking characteristics of AIDS are the decrease in helper T lymphocytes (TR), and a steady decrease in the ratio of T4 to suppressor T lymphocytes (T8), i.e., T4/T8, as the disease progresses.

AIDS was first reported in the United States of America in 1981, and it has been estimated that today there are more than 20,000 AIDS patients in the U.S.A. alone. At least around 50,000 people have died of the disease as of March, 1988. Carriers of the virus have been estimated to number one million persons in the U.S.A. In addition to the U.S.A., there are also many AIDS victims in Africa and Europe, and there is a huge amount of research being carried out today to develop methods for the diagnosis, prevention and treatment of AIDS.

HIV, the causative agent of AIDS, is a retrovirus. This virus has been shown to be composed of RNA consisting of about 9,700 base pairs, three gag proteins (having molecular weights of 55,000, 24,000 and 17,000 daltons), a reverse transcriptase (molecular weights of 66,000 and 51,000 daltons have been detected), three glycoproteins (two molecules having molecular weights of 120,000 and 41,000 daltons, and their precursor, a molecule with a molecular weight of 160,000 daltons; these glycoproteins are hereinafter abbreviated as gp120, gp41 and gp160) which comprise the viral envelope, and other components. Especially from the viewpoints of viral infection and its prevention, the envelope, which is exposed on the surface of HIV, carries particular importance. As a result of proteolysis, gp160 is cleaved into gp120 and gp41. As shown in FIG. 1, gp41 is a transmembrane protein which is incorporated into the lipid bilayer of the viral envelope, while gp120 is exposed on the outside of the envelope and some of it is released from the virus. Both gp41 and gp120 possess many sugar-binding sites, and about half of the gp120 molecule is comprised of sugars. The gp120 molecule binds to, or near to, the CD4 antigens which exist on the cell surface of helper T cells, etc., and in addition to bringing about infection of the cells by the virus, gp120 possesses activity which results in syncytium formation in the cells. gp120 is described in greater detail in U.S. Pat. No. 4,725,669.

In light of the above background information regarding HIV and AIDS, it is clear that antibodies specific for the envelope of the virus, which plays such an important role in the establishment of the viral infection, have great significance in the prevention of the infection.

M. Robert-Guroff et al. (J. Immunol. 138: 3731, 1987) reported that the progression of the disease was slower in patients whose blood contained viral-neutralizing antibodies in comparison with patients not having such antibodies. In addition, it has been reported that the neutralizing antibodies in the blood of AIDS patients bind to gp120 (L. A. Lasky et al.: Science 233: 209, 186; and T. J. Mathew et al.: Pro. Natl. Acad. Sci. U.S.A. 83: 9709, 1986). In light of these findings, it is clear that antibodies specific for gp120 must play an important role in the prevention of infection by HIV.

A number of research groups have already reported successful development of a mouse MCA specific for gp120. For example, T. C. Chanh et al. (Eur. J. Immunol. 16: 1465, 1986) reported that they chemically synthesized a portion of the peptide chain of gp120 and then prepared an MCA specific for that synthetic peptide. They employed that MCA in the indirect fluorescent antibody technique and reported that they were able to detect HIV infection with greater sensitivity than was possible with the reverse transcriptase determination technique. In addition, Gosting et al. (J. Clin. Microbiol.: 25, 845, 1987) reported that they solubilized HIV viral antigens, adsorbed them to a column of lentil lectin-Sepharose 4B, collected the glycoprotein fraction thereof and used it to immunize mice, and succeeded in producing an anti-gp120 mouse MCA and an anti-gp41 mouse MCA. Matsushita et al. (Medical Immunol. 14: 307, 1987) also reported achieving viral neutralization with an anti-gp120 mouse MCA. These MCAs are useful in the diagnosis of HIV infection. However, unfortunately, they are unsuited for the tasks of prevention of HIV infection and treatment of established disease (ARC and AIDS), since these MCAs are mouse proteins, and therefore they are recognized as foreign by the human immune system if they are administered to the human body. As a result, not only would the MCA activity be inhibited by the anti-mouse MCA antibodies that would be produced by the human immune system, but anaphylactic side effects would also occur. Therefore, it is clear that for the prevention and treatment of HIV infection in man, it is necessary to develop an MCA of human origin, rather than an MCA of mouse origin.

In general, human-origin anti-HIV MCAs can be produced by (1) hybridomas obtained by fusion of human B lymphocytes having the ability to produce antibodies specific for HIV and cells of established lymphoid cell lines such as myeloma cells, and (2) lymphoblastoid cells obtained by Epstein-Barr (EB) virus-induced transformation of human B lymphocytes having the ability to produce antibodies specific for HIV. From about 1980 up to the present time, much research has been carried out on the production of human MCAs, but none of those efforts have led to an established method such as in the case of mouse MCAs because each of the approaches described above has its own special problems.

In 1987, there were two reports concerning human MCAs specific for HIV. One was by L. Evans et al. (Proceedings of the Third Congress on AIDS, TP130, 1987). Evans et al. employed EB virus to transform lymphocytes from HIV-infected patients and obtained a human MCA which reacted with gag proteins having molecular weights of 55, 41 and 25 kilodaltons. That human MCA belonged to the IgG4 subclass, and it did not neutralize HIV. The second report was by B. Banapour et al. (ibid, TP114). Banapour et al. also employed EB virus to transform lymphocytes from anti-HIV antibody-positive subjects, fused the transformed cells with heteromyeloma cells, and obtained a human MCA which reacted with gp41. This MCA was IgG, but the subclass was not reported. This MCA also did not show HIV-neutralizing activity. Thus, in both of those reports, transformation by EB virus was employed. This technique, because it is very efficient at achieving immortalization of human B lymphocytes, is far superior to the cell fusion method. Nevertheless, the obtained lymphoblastoid cell lines produce EB virus, or even if they do not produce the virus particles, they contain the EB viral DNA which carries the potential for production of the virus. EB virus has the ability to transform lymphocytes, which means that this virus has tumorigenicity. Therefore, there is worry concerning the safety of using this EB virus transformation technique to produce a drug product for administration to humans.

It is known that lymphoblastoid cells resulting from transformation of lymphocytes by EB virus can be further infected by HIV, and thus, there is a fear that a cell line producing a human MCA might be infected by both EB virus and HIV. In addition, antibody production by lymphoblastoid cell lines presents some disadvantages in view of the facts that it is usually lower and also less stable than the level of production by hybridomas. The reason that Banapour et al. performed additional cell fusion of lymphoblastoid cell lines was to attempt to improve the antibody producing ability of those cell lines.

Accordingly, as seen above, if the immortalization of human B lymphocytes could be achieved with greater efficiency by cell fusion and if a hybridoma having the ability to produce a human MCA specific for HIV could be obtained, then the resultant hybridoma would be very desirable on the basis of its having high productivity of an MCA which would moreover be safe for use as a drug.

However, both of the two above-mentioned human MCAs obtained by Evans et al. and Banapour et al. are specific for gag proteins and gp41. The gag proteins are located inside the viral particles, and are not exposed on the viral surface. In the case of HIV-infected cells, as well, those proteins are located inside the cell, not on the surface. Accordingly, MCAs which are specific for gag proteins will be able to bind to gag proteins shed by viral particles or released from ruptured viral particles, but they will not be able to bind to intact viral particles or infected cells. For this reason, it is not expected that such MCAs will provide any protective effect against infection by the virus. Similarly, gp41 is located relatively close to the surface of viral particles and infected cells, but it is a transmembrane protein which is embedded in the surface membrane and it is thus difficult for MCAs to bind to gp41.

Therefore, for the purpose of preventing infection of cells by HIV, it is clear that the most suitable type of human MCA would be one which is specific for gp120, a glycoprotein which is exposed on the surface membrane of the viral particles, has activity in binding to the host cells and is expressed on the surface of infected cells.

In addition, with regard to the subclass which would be the most desirable for human MCAs, it is evident that it would be advantageous for the antibody to be of a subclass which possesses the ability to activate complement and the ability to bind to the Fc receptors on macrophages and lymphocytes. It has been demonstrated that activation of complement by the classical pathway can be achieved by the IgG1 and IgG3 subclasses, whereas IgG2 and IgG4 cannot achieve this activation (J. L. Winkelhake: Immunochem. 15: 695, 1978). Furthermore, it has also been shown that the IgG1 and IgG3 subclasses have a strong affinity for the Fc receptors of monocytes (Cosio et al.: Immunol. 44: 773, 1981). Therefore, to prevent infection of cells, it is clear that the IgG1 and IgG3 subclasses are desirable.

However, another consideration is that of purification of the human MCA. Affinity chromatography using protein A is known to be effective for the purification of MCAs, and since IgG1 binds to protein A, whereas IgG3 does not, it is clear that the IgG1 subclass of human MCAs are the most desirable subclass from the viewpoint of ease of purification.

SUMMARY OF THE INVENTION

It is therefore an object of the present invention to provide a human monoclonal antibody which is capable of binding to HIV and neutralizing it.

It is yet another object of the present invention to provide human monoclonal antibodies which belong to the IgG1 subclass and are specific for HIV.

It is yet another object of the present invention to provide a human monoclonal antibody having a subclass of IgG1 and which recognizes and binds to gp120, gp160, and/or gp41.

It is yet another object of the present invention to provide a method for producing human monoclonal antibodies, which does not involve transformation by Epstein-Barr virus.

These and other objects of the present invention which will hereinafter become more readily apparent, have been achieved by fusing mouse myeloma cells and lymphocytes from the lymph nodes of HIV-seropositive donors, under carefully controlled conditions, to produce human monoclonal antibodies having the IgG1 subclass, and which are capable of neutralizing HIV.

To date, no one has recognized that one could produce human IgG1 monoclonal antibodies which are capable of neutralizing HIV. In view of the discovery of this possibility in the present invention, and following the techniques described herein, one can obtain IgG1 human monoclonal antibodies with HIV neutralizing activity, and therefore, in general, these monoclonal antibodies along with the hybridomas producing them are within the scope of the present invention.

DETAILED DESCRIPTION OF THE PREFERRED EMBODIMENTS

Figure 1:
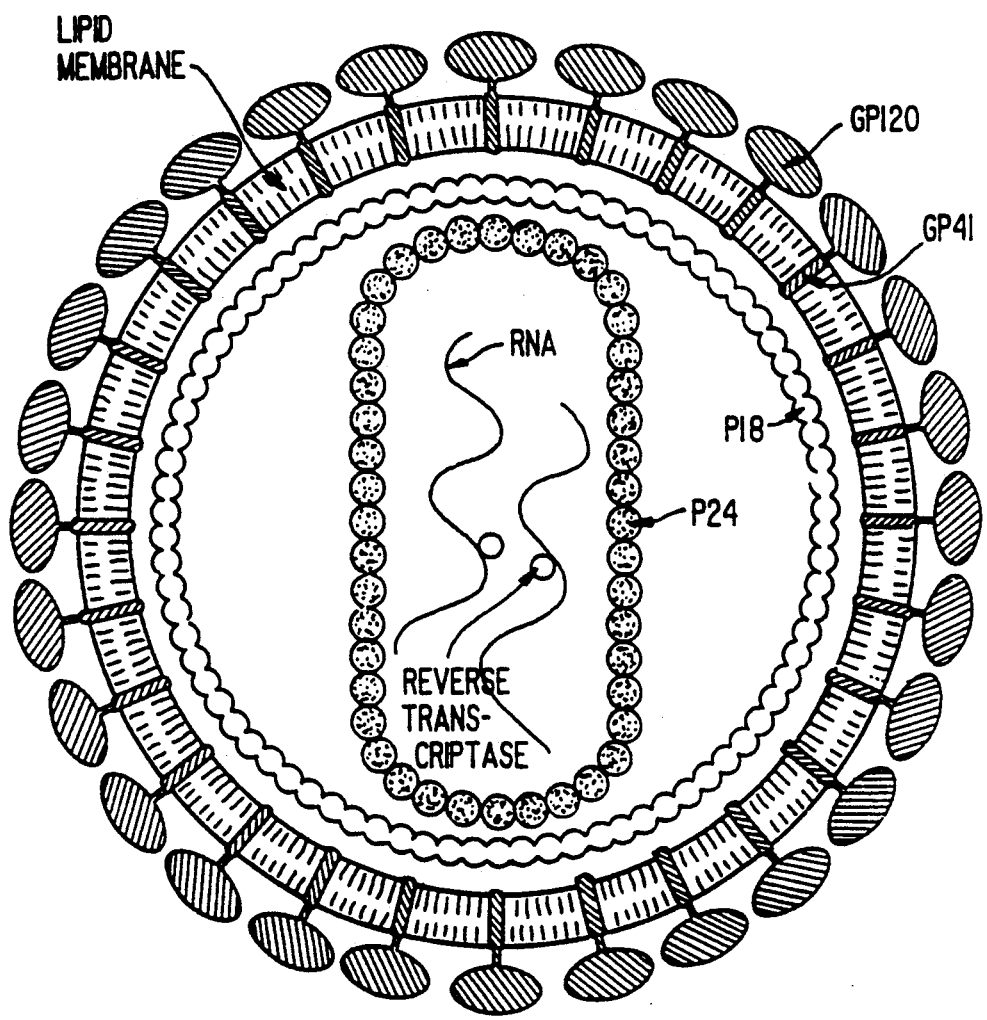
FIG. 1 shows a schematic cross-sectional view of an HIV viral particle.

As a result of carrying out vigorous research aimed at obtaining an anti-HIV human MCA and employing a method involving fusion of mouse myeloma cells and lymphocytes from the lymph nodes of HIV-seropositive donors, the present inventors succeeded in obtaining a hybridoma which produces a human MCA (IgG1 subclass) specific for gp120 and a hybridoma which produces a human MCA (IgG1 subclass) reacting with both gp120 and gp41. They also succeeded in culturing the hybridomas and/or cell lines originating from the hybridomas and were able to collect the anti-HIV human MCAs from the supernatants of the cell cultures.

That is, the present invention is directed to human monoclonal antibodies which are specific for HIV and belong to the IgG1 subclass, specifically an IgG1 antibody which binds with gp120 of HIV, and also an IgG1 antibody which binds with both gp120 and gp41 of HIV. In addition, this invention is directed to hybridomas which produce such human monoclonal antibodies, which are formed by fusion between human lymphocytes and mouse myeloma cells. Two such hybridomas were deposited at the American Type Culture Collection, 12301 Parklawn Drive, Rockville, Md. 20852, U.S.A. on Mar. 25, 1988 and have been assigned the accession numbers HB9670 and HB9669.

Another aspect of this invention is the method by which the inventors succeeded in efficiently forming the above described hybridomas. In this method, human lymphocytes were first treated with complement and an anti-human T-lymphocyte mouse MCA and then the treated human lymphocytes were subjected to fusion with mouse myeloma cells. Other details of this process are discussed hereinbelow.

The human lymphocytes employed in the method of this invention can be obtained from the spleen, lymph nodes, peripheral blood, bone marrow, tonsils, adenoids, etc., of HIV seropositive donors. It is preferred that the lymphocytes be obtained from the lymph nodes, spleen or tonsils of HIV seropositive donors or patients with lymphadenopathy.

As the mouse myeloma cells, it is advantageous to employ a cell line which is resistant to 8-azaguanine, and the following are some of the publicly-known cell lines from BALB/c mice: P3x65Ag8, P3-NS1/1-Ag4-1, P3x63AgU1, SP2/0Ag14, P3x63Ag8 6.5.3, MPC11-45.6.TG1.7 and SP-1. A preferred mouse myeloma cell line is P3x63AgU1. It is described in U.S. Pat. No. 4,363,799, which is incorporated herein by reference.

In the method of this invention, prior to the fusion of the human lymphocytes and the mouse myeloma cells, it is preferable to first treat the human lymphocytes with complement and an anti-human T-lymphocyte mouse MCA (e.g., OKT3, a product of Ortho Diagnostics Co., Ltd.) so as to eliminate the human T-lymphocytes. In the actual performance of the method of this invention, for example, a fixed lymphatic tissue is surgically excised from a seropositive human donor and gently dissected with scissors and a scalpel to obtain a liquid containing suspended cells. This suspension is then layered onto a Ficoll-Paque® solution, and the lymphocytes are separated and harvested by centrifugation. Then, the lymphocytes are treated with 0.5 ml of fresh serum as the source of complement and 1.0 ml of an anti-human T-lymphocyte mouse MCA to destroy the T-lymphocytes. The efficiency of hybridoma formation is increased by this procedure.

The thus-obtained human lymphocytes are then fused with mouse myeloma cells. The general conditions for cell fusion and culture of hybridomas are already known, but the inventors nevertheless carried out vigorous research to determine the specific combinations which enhance formation and propagation of hybridomas. As a result, the inventors were able to achieve formation of one hybridoma for every $10^4$ lymphocytes treated by the method of this invention.

The preferred conditions were determined to be as follows. For example, lymphocytes and mouse myeloma cells are mixed at a ratio of 10:1 to 1:100, preferably 1:1 to 1:10. A suitable solution for cell fusion, such as RPMI 1640 containing ca. 35% (e.g., 25-45%) polyethyleneglycol (molecular weight: about 1,000-6,000) and ca. 7.5% (e.g., 5-10%) dimethylsulfoxide is added. The resulting cell suspension is stirred for one to several (e.g., 10-30) minutes at a temperature in the ambient (25° C.) to 37° C. range, and then the suspension is gradually diluted and washed with RPMI 1640 containing 10% fetal calf serum (FCS). Finally, the suspension is further diluted with HAT (hypoxanthine-aminopterin-thymidine) selective culture solution to give a cell density of $1-5\times 10^5$/ml. Mouse peritoneal exudate cells are added to a 96-well plate as a feeder layer, and the culture solution is removed immediately before the fused cells are introduced by dispensing 0.2 ml aliquots of the suspension into the wells of the plate. These are then cultured for 3-4 weeks at 35°-38° C. in humidified air containing about 5% $CO_2$ (e.g., 2-7% $CO_2$). Only hybridoma cells are present in the HAT culture solution, since the 8-azaguanine-resistant myeloma cells and cells arising from fusion of myeloma cells cannot survive in the HAT solution (unfused antibody-producing cells die within a few days).

After culturing the hybridomas in the 96-well plates, the antibody titer of the culture fluid of each well containing cells is determined by the enzyme-linked immunosorbent assay (ELISA) technique, and only hybridomas which produce the desired antibodies are selected. Cells of each selected hybridoma are collected, cloning is performed by the limiting dilution method, and subclones which stably produce an MCA are established. Then the hybridomas are further investigated by analyzing the antigens recognized by the MCAs they produce by a Western blot analysis technique, and investigating the ability of the produced MCAs to bind to the surface of HIV-infected cells. Hybridomas which produce an MCA which binds to gp120 and which can bind to the surface of infected cells are finally selected.

The mouse-human hybridomas which were obtained by the method of this invention as described above and which produce anti-HIV human MCAs can be preserved by freezing. If these hybridoma cell lines and/or cell lines derived from them are cultured on a large scale by an appropriate method, it is possible to obtain from the culture supernatant human MCAs of the present invention. In addition, if these hybridomas are transplanted into animals to form tumors, the produced human MCAs can be obtained from the ascites or the serum of the animals.

Two of the anti-HIV human MCAs which have been obtained by the methods described above and which have been deposited at the ATCC, have the following characteristics:

(1) In ELISA using fixed viral antigens obtained from HIV-infected cells, the MCAs were positive for binding, but they were negative for binding in an ELISA using plastic coated with substances obtained from uninfected cells by the same technique.

(2) Since HIV is composed of many antigenic substances, a Western blot analysis technique was applied to determine the nature of the structural components to which the human MCAs obtained in this invention bind. It was thus found that one of the human MCAs binds to a molecule having a molecular weight of 120 kilodaltons (120 Kd) and to a molecule having a molecular weight of 160 Kd (160 Kd is the precursor of 120 Kd and 41 Kd molecules). The second MCA was found to bind to molecules having molecular weights of 41 Kd, 120 Kd and 160 Kd.

(3) The MCAs were investigated to determine whether or not they bind to the surface of HIV-infected cells. After the human MCA was reacted with unfixed HIV-infected cells, fluorescein-labeled antibody to human IgG was allowed to react, and strong fluorescence was observed on the surface of the infected cells. Therefore, it was determined that both the human MCAs of this invention bind to the surface of infected cells.

(4) Human IgG is known to have four subclasses, IgG1, IgG2, IgG3 and IgG4, with each subclass having its own characteristic biological activities. The subclass of each of the two specific anti-HIV human MCAs described herein was thus investigated using a specific animal antiserum, and it was found that both of the MCAs described herein belong to the IgG1 subclass.

Although only two specific hybridomas have been deposited in connection with the present invention, it will be appreciated that by following the above described methods, as illustrated in the examples hereinbelow, one of ordinary skill in the art could obtain additional IgG1 subclass human monoclonal antibodies with HIV neutralizing ability. To fall within the scope of the present invention, these monoclonal antibodies will be both of the IgG1 subclass, and will recognize and bind to one or more of the viral envelope proteins of HIV. These proteins include gp120, gp160 and gp41, which are described hereinabove.

EXAMPLES

Example 1

A. Cell Fusion

1. Collection of Lymphocytes

A lymph node which was surgically excised from an ARC patient was finely minced using scissors and scalpel. Cells obtained therefrom were suspended in medium A (RPMI 1640 containing 10% fetal calf serum (FCS), 2 mM glutamine, 1 mM sodium pyruvate, 20 $\mu$g/ml L-serine, 0.05 u/ml human insulin and 80 $\mu$g/ml gentamicin sulfate). This cell suspension was layered onto a Ficoll-Paque ® solution and centrifuged at 1,500 rpm for 20 min. The cells which collected on the top of the Ficoll-Paque ® were harvested, centrifugally washed once with phosphate-buffered saline (PBS) and twice with RPMI 1640. Finally, the cells were resuspended in RPMI 1640 to a concentration of $1 \times 10^7$ cells/ml.

2. Treatment of Lymphocytes

To reduce the amount of cell fusion that would take place with T lymphocytes, the T lymphocytes in the lymphocyte suspension were eliminated. That is, OKT3 (Ortho Diagnostics Co., Ltd.) was added to the abovementioned cell suspension to give a final 200-fold dilution. After reacting this at 4° C. for 60 min, the cells were precipitated by centrifugation (1,500 rpm for 5 min). Next, baby rabbit complement was diluted 3-fold (with RPMI 1640) and added to the cell pellet to suspend it; this was then reacted at 37° C. for 60 min. Then this cell suspension was twice subjected to centrifugal washing.

3. Cell Fusion

The OKT3-treated lymphocytes and untreated lymphocytes were each mixed with mouse myeloma P3U1 cells (both cell populations were $3 \times 10^7$ cells) in RPMI 1640 medium. These cell mixtures were then precipitated by centrifugation (1,600 rpm, 5 min). The supernatant was discarded, and the cell pellet was broken up by tapping the tube. Then 1 ml of polyethylene glycol solution (35% v/v polyethylene glycol No. 1000 and 7.5% v/v dimethylsulfoxide in RPMI 1640) was slowly added to the tube, and this was allowed to stand for one min at room temperature. Next, 2 ml of RPMI 1640 was added, and the mixture was allowed to stand for one min; another 2 ml of RPMI 1640 was added, and the mixture was allowed to stand for an additional 2 min. Then 4 ml of HAT medium (95 $\mu$M hypoxanthine, 0.4 $\mu$M aminopterin and 16 $\mu$M thymidine in medium A) was added, and the mixture was allowed to stand for 2 min; another 8 ml of HAT medium was added and it was allowed to stand for 2 min; an additional 24 ml of HAT medium was added and it was allowed to stand at 37° C. for 30 min. Finally, the total volume was made up to between 75 and 150 ml by the addition of HAT medium.

Aliquots of approximately 200 $\mu$l were seeded into the wells of a 96-well flat culture plate. This culture plate had been pretreated by seeding ICR mouse (male) peritoneal exudate cells at $2 \times 10^4$ cells/well; immediately prior to the seeding of the fused cells, the culture fluid was removed from the wells. This culture plate was then incubated at 37° C. in a $CO_2$ incubator. Once per week, half of the culture medium in each well was replaced by HT medium (HAT medium from which aminopterin had been left out), and the incubation was continued until hybridoma colonies became apparent.

4. Cloning

At the time when hybridoma colonies became apparent, each of the culture fluids was tested for the presence of antibody activity towards HIV. The hybridomas of colonies which were found to be producing HIV-specific antibodies were then cloned. First, 96-well flat plates were seeded with only mouse peritoneal exudate cells at $2 \times 10^4$ cells/well. Then, at various times from one hr to one day after the seeding, the culture medium was removed and the hybridomas were seeded into 48 wells each at 10 cells/well. For the first cloning, HT medium was employed, while medium A was used for the second cloning. After 2-3 weeks of culture, the antibody activity was determined, and positive clones were collected.

B. ELISA (Enzyme-Linked Immunosorbent Assay)

1. Viral Antigens a. HTLV-III (human lymphotropic virus type III) antigen (Bionetics Laboratory Products Co., Ltd.)

b. CR10/NIT Antigen

CR10/NIT is a cell line which was established by creating a persistent infection of CEM cells with the NIT strain of HIV. The viral antigens were partially purified from this CR10 cell line. In brief, CR10/NIT cells were washed 3 times with PBS and then frozen at $-70°$ C. At the time of use, the frozen cells were thawed, and $10^8$ cells were suspended in 9 ml of distilled water; this cell suspension was vigorously agitated for one min using a Vortex blender. This was then centrifuged for 10 min at 2,800 rpm, and the supernatant was collected. One ml of 10-fold concentrated PBS was next added to the supernatant, centrifugation was performed at $15,000 \times g$ for 30 min, and the pellet was collected. The pellet was resuspended in 5 ml of PBS, sonicated 4 times for 15 sec each while chilling in ice and allowed to stand for a further 30 minutes while chilling in ice; the supernatant was then collected. The supernatant was subjected to ultracentrifugation at $100,000 \times g$ for one hr, and the supernatant was employed as the viral antigen preparation. As the negative control, an antigen preparation was obtained by treating CEM cells (uninfected by HIV) in the same manner.

2. Antigen-Coated Plates

HTLV-III antigen (1 μg/ml), CR10/NIT (20–25 μg/ml) and CEM antigens (20–25 μg/ml) were each dispensed in aliquots of 50 μg to the wells of separate microtiter plates (Coster, No. 3912), and the plates were then allowed to stand at 37° C. for 60 min. The plates were then washed twice with HBSS-BSA (Hank's balanced salt solution, 0.5% bovine serum albumin and 0.1% $NaN_3$), PBS ($Ca^{2+}$, $Mg^{2+}$) containing 3% BSA was dispensed at 125 μl/well, and the plates were allowed to stand at 37° C. for 60 min and then at 4° C. overnight to carry out blocking.

3. ELISA

The antigen-coated plates were washed twice with HBSS-BSA, and then 50 μl of each of the heated (56° C. for 60 min) hybridoma culture fluids was added. After letting these react at room temperature for 60 min, the plates were again washed twice with HBSS-BSA. Then 50 μl of alkaline phosphatase-conjugated goat antibody to human IgG (diluted 1000×; Tago Inc.), and reaction was again allowed to take place at room temperature for 60 min before the plates were washed 4 times with HBSS-BSA. Next, 100 μl of 0.05M carbonate buffer containing 1 mg/ml p-nitrophenylphosphate and 1 mM $MgCl_2$, pH 9.5, was added to each well, and the plates were reacted at room temperature for 60 minutes or overnight. Finally, the optical density was measured at 495 nm using an ELISHA Reader (Titertech Inc.).

C. Results

1. Lymph node cells from Patient A were compared with and without OKT3 treatment.

TABLE 1

| | Generation of Hybridomas Producing IgG Antibodies to HIV* | | |
|---|---|---|---|
| | Number of Anti-HIV IgG-Positive Wells | | |
| Treatment | high O.D.** | medium O.D. | low O.D. |
| − OKT3 | 3 | 2 | 1 |
| + OKT3 | 6 | 5 | 6 |

*Indicates wells containing hybridomas which produce IgG that reacts with CR10/NIT antigens but not with negative control (CEM antigens).
**"High" means that the optical density at 495 nm was larger than 1.0, while "medium" indicates 0.4–1.0 range and "low" represents 0.2–0.3 range. Therefore, more hybridomas producing IgG antibodies to HIV were generated in the case of the lymphocytes which were treated with complement and anti-lymphocyte antibody.

2. As reported above, hybridomas were obtained by fusion of mouse myeloma cells with OKT3-treated lymphocytes from the lymph nodes of patients with ARC, the hybridomas were cloned, and the inventors successfully established hybridomas No. 86 and No. 1, which stably produce MCAs. In ELISA, the MCAs produced by hybridomas No. 86 and No. 1 reacted with HTLV-III antigen and CR10/NIT antigens but not with CEM antigens. The MCA production rates were 10 μg/$10^6$ cells/day in the case of No. 86, and 20 μg/$10^6$ cells/day in the case of No. 1.

Example 2

A. Purification of MCAs

The culture fluids (1.5–2 liters) of hybridomas No. 86 and No. 1 were used as the starting materials. Ammonium sulfate was added to the culture fluids to 50% saturation, and the resultant precipitates were collected by centrifugation at 10,000 rpm for 30 min. The precipitates were then dissolved in a suitable volume of PBS, followed by dialysis against PBS. The dialyzed solution was next applied to a protein A-Sepharose column bed (bed volume: 6 ml; Pharmacia AB). The column was washed with saline, and then the IgG was eluted with HCl in saline (pH 2.5). The IgG eluted in this manner was confirmed to be pure by sodium dodecyl sulfate-polyacrylamide gel electrophoresis (SDS-PAGE).

B. Identification of IgG Subclasses of MCAs

1. Heavy Chains

The purified MCA solutions were reacted with sheep antisera to human IgG1, IgG2, IgG3 and IgG4 (Serotec Inc.). The subclass of each MCA was identified on the basis of which antisera resulted in formation of an immunoprecipitation ring. It was thus found that both No. 86 and No. 1 MCAs reacted only with the anti-IgG1 and did not react with the other three antisera. Therefore, both of these anti-HIV MCAs were identified to be IgG1.

2. Light Chains

A microtiter plate was coated with goat antibody to human IgG (Tago Inc.). Each of the purified MCAs was then reacted with this anti-human IgG-coated plate. Next, in accordance with the method for ELISA described above in section B. of Example 1, alkaline phosphatase-conjugated goat antibodies to human lambda chain and to kappa chain (Tago Inc.) were employed and the type of each MCA was identified. As a result, No. 86 MCA was shown to have a kappa chain, while No. 1 MCA was found to have a lambda chain.

C. Viral Antigens Recognized by the MCAs

The Western blot method (Bio Rad Immunoblot Assay; Bio Rad Inc.) was employed to identify which viral antigens were recognized by MCAs No. 86 and No. 1. MCA No. 1 has also been referred to as MCA 1.2 by the inventors; thus, MCA 1 and MCA 1.2 refer to the same cell line. The procedures of the assay technique are briefly described as follows.

Figure 2:
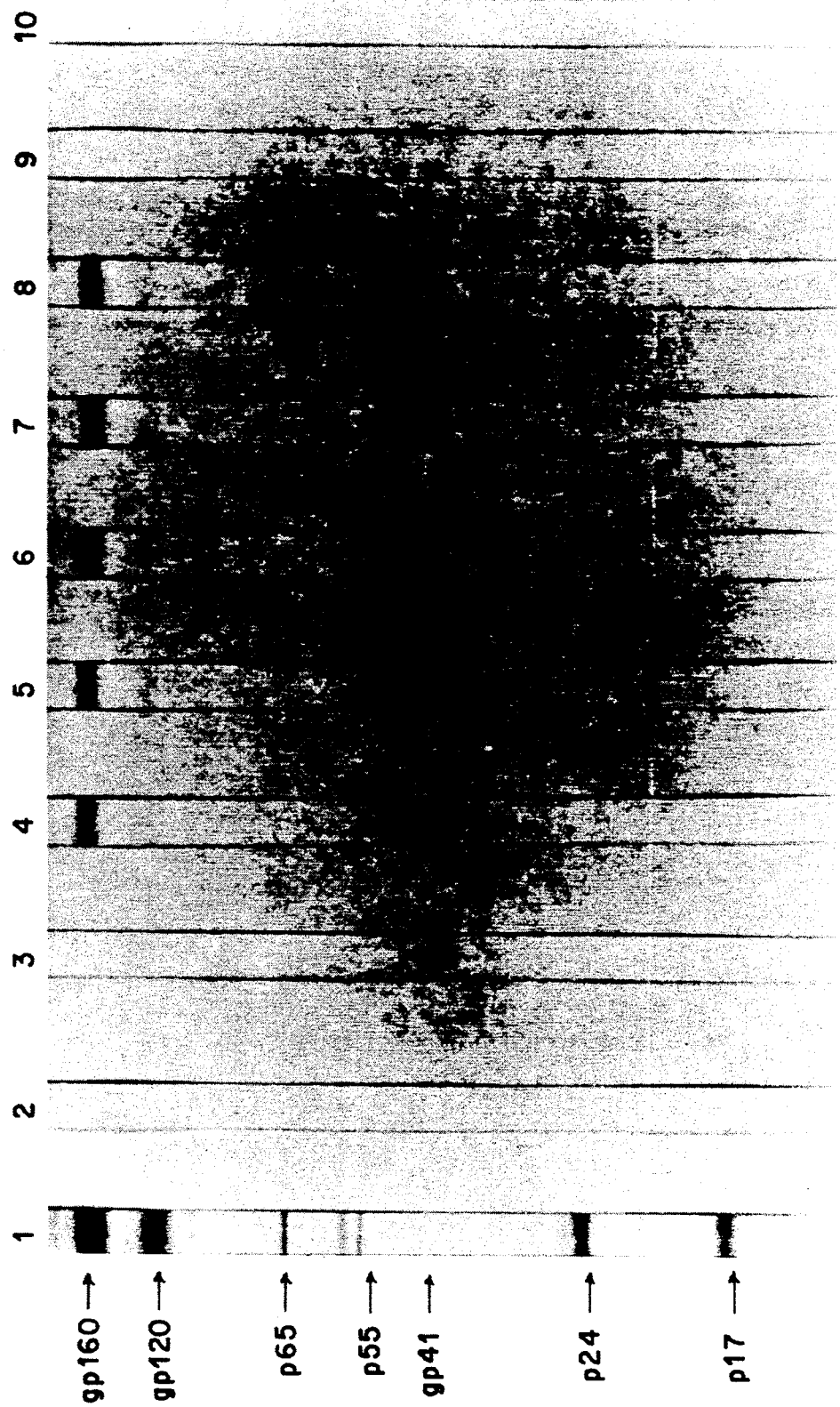
FIG. 2 shows the results of Western blot analysis of two of the MCAs of the present invention.

The HTLV-III strain of HIV was applied to SDS-PAGE, the separated viral antigens were blotted on nitrocellulose strips, and each of the semi-purified MCAs was reacted thereon. Next, peroxidase-conjugated antibody to human IgG was reacted with the strips, and finally, to develop color, an enzyme substrate was reacted with the strips. The results are shown in FIG. 2. In the figure, strip number 1 is serum from an AIDS patient, strip numbers 2-3 are serum from a normal human, strip numbers 4-5 are subclones 1 of No. 86, strip numbers 6-8 are subclones 2 of No. 86, and strip numbers 9-10 are subclones of No. 94.

MCA No. 86 reacted strongly with gp41, and reacted weakly with gp120. As the reason for reacting with both gp41 and gp120, it was possible that MCA No. 86 was a mixture of one MCA which reacted with gp41 and another MCA which reacted with gp120. To investigate this possibility, the hybridoma producing MCA No. 86 was again cloned, yielding subclones 1, 2, 3 and 4, and the MCA produced by each of those subclones was also subjected to the Western blot assay. Again, as can be seen in FIG. 2, the MCA from each of the 4 subclones of hybridoma No. 86 reacted with both gp41 and gp120. This finding suggests that MCA No. 86 either recognizes an antigenic epitope which is present on both gp41 and gp120, or is an antibody directed at the cleavage site of gp41 and gp120. MCA No. 86 also reacted with gp160, and the reason for this is that this antigen is a glycoprotein constructed from gp41 and gp120.

MCA No. 1 reacted with gp120. It, of course, also reacted with gp160, which is the precursor of gp120.

D. Binding to the Surface of HIV-Infected Cells

The ability of MCAs No. 86 and No. 1 to bind to the surface of HIV-infected cells was investigated by the indirect fluorescent antibody technique.

C-3 cells (an HTLV-III transformed cell line), $5 \times 10^6$ cells, were mixed with $2.5 \times 10^6$ $TCID_{50}$ of HTLV-IIIb, and this mixture was incubated at 37° C. for 2 hr to permit infection to proceed. These cells were then cultured for 3 days in RPMI 1640 medium containing 20% FCS, following which the cells were washed 3 times at 4° C. with PBS containing 0.1% $NaN_3$. As the negative control, C-3 cells which were not infected with HIV were employed.

These unfixed cells were dispensed into conical tubes to give $2 \times 10^6$ cells/tube, and centrifugation was performed at 1,500 rpm for 5 min. The supernatant was discarded, and the cell pellet was suspended in 50 $\mu$l of 0.1% $NaN_3$—HBSS. This suspension was reacted at 4° C. for 60 min, and then the cells were washed 3 times with 0.1% $NaN_3$—1 mM EDTA-PBS. Each cell pellet was suspended in 100 $\mu$l of fluorescein isothiocyanate-labeled antibody to human IgG (50×dilution; Tago Inc.), followed by reaction at 4° C. for 60 min.

The cells treated as above were next analyzed by flow cytometry (FAC Scan; Becton Dickinson Co.). Binding was investigated for the following combinations: HTLV-IIIb-infected C-3 cells and serum (100×diluted) from an AIDS patient, uninfected C-3 cells and serum (100×diluted) from an AIDS patient, HTLV-IIIb-infected C-3 cells and serum (100×diluted) from a normal adult, uninfected C-3 cells and serum (100×diluted) from a normal adult, HTLV-IIIb-infected C-3 cells and MCA No. 86, uninfected C-3 cells and MCA No. 86, HTLV-IIIb-infected C-3 cells and MCA VI, and uninfected C-3 cells and MCA VI. VI was an IgG human MCA specific for an irrelevant antigen.

The following results were obtained. MCA No. 86 bound to the surface of HIV-infected cells, but it did not bind to the uninfected cells. The same results were obtained with MCA No. 1. MCA VI, which was not specific for HIV, did not react with the HIV-infected cells.

With an MCA which reacts with the surface of HIV-infected cells, it might be possible to destroy HIV infected cells in the presence of complement or in the presence of lymphocytes or macrophages, thereby stopping the production of new virus and permitting suppression of the spread of the infection.

The results of the various experiments described above are compiled in the following Table 2.

TABLE 2

| Property | MCA No. 86 (HB 9669) | MCA No. 1 (1.2) (HB 9670) |
|---|---|---|
| Isotype | IgG1; kappa chain | IgG1; lambda chain |
| Binding to HIV in ELISA | HTLV-IIIb CR10/NIT | HTLV-IIIb CR10/NIT |
| Viral antigens recognized | gp41, gp160 (gp120, weak) | gp120, gp160 |
| Binding to HIV-infected cells | positive | positive |
| MCA production rate | 10 $\mu$g/$10^6$ cells per day | 20 $\mu$g/$10^6$ cells per day |
| Stability of MCA production | $\geq$ 6 months | $\geq$ 4 months |

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A hybridoma having all of the identifying characteristics of the hybridoma designated MCA 86 having A.T.C.C. Accession No. HB 9669.

2. A human monoclonal IgG1 antibody produced by the hybridoma of claim 1.

* * * * *

UNITED STATES PATENT AND TRADEMARK OFFICE
CERTIFICATE OF CORRECTION

PATENT NO. : 5,298,419
DATED : March 29, 1994
INVENTOR(S) : Yasuhiko MASUHO, et al.

It is certified that error appears in the above-indentified patent and that said Letters Patent is hereby corrected as shown below:

On the title page, Item [75], the 5th inventor's last name should read as follows:

--Petersen--

Signed and Sealed this

Twelfth Day of July, 1994

Attest:

BRUCE LEHMAN

Attesting Officer

Commissioner of Patents and Trademarks